United States Patent [19]

Subramanian

[11] Patent Number: 5,073,368

[45] Date of Patent: Dec. 17, 1991

[54] SANGUINARIA MOUTHRINSE HAVING IMPROVED ANTI MICROBIAL ACTIVITY AND STABILITY

[75] Inventor: Malathy Subramanian, Somerset, N.J.

[73] Assignee: Colgate-Palmolive Company, Piscataway, N.J.

[21] Appl. No.: 699,878

[22] Filed: May 15, 1991

[51] Int. Cl.⁵ .......................... A61K 7/16; A61K 7/26
[52] U.S. Cl. ........................................ 424/58; 424/49; 424/54
[58] Field of Search ...................... 424/49-58

[56] References Cited

U.S. PATENT DOCUMENTS

| 4,117,107 | 9/1978 | Shapiro et al. | 424/49 |
|---|---|---|---|
| 4,117,108 | 9/1978 | Shapiro et al. | 424/49 |
| 4,130,637 | 12/1978 | Bauman | 424/54 |
| 4,145,412 | 3/1979 | Ladanyi | 424/58 |
| 4,335,110 | 6/1982 | Collins | 424/58 |
| 4,590,061 | 5/1986 | Southard | 424/58 |
| 4,666,517 | 5/1987 | Bakar | 424/52 |
| 4,689,216 | 8/1987 | Greene | 424/58 |
| 4,774,078 | 9/1988 | Curtis et al. | 424/49 |
| 4,863,722 | 9/1989 | Rosenthal | 424/49 |
| 4,911,927 | 3/1990 | Hill et al. | 424/443 |
| 4,919,939 | 4/1990 | Baker | 424/493 |

FOREIGN PATENT DOCUMENTS 396232 11/1990 European Pat. Off. .
8704922 8/1987 PCT Int'l Appl. .

OTHER PUBLICATIONS

Donohue et al, CA 115:35519w (1990) of E.P. 396232 11/07/90.
Michaels CA. 108:118759F (1987) of WO/PCT 8704922 8/27/87.
Bauman CA. 90:157080g (1978) of U.S. Pat. No. 4,130,637, 12/19/78.

Primary Examiner—Shep K. Rose
Attorney, Agent, or Firm—Paul Shapiro; Robert C. Sullivan

[57] ABSTRACT

Mouthrinses containing sanguinaria of improved anti microbial efficacy and stability are attained by including in the mouthrinse a surfactant combination of an amidobetaine and poly(oxyethylene)-poly(oxypropylene) block copolymer.

9 Claims, No Drawings

SANGUINARIA MOUTHRINSE HAVING IMPROVED ANTI MICROBIAL ACTIVITY AND STABILITY

FIELD OF THE INVENTION

This invention relates to novel sanguinaria based mouthrinses having improved antimicrobial activity, sanguinaria stability and release.

BACKGROUND OF THE INVENTION

Sanguinarine canadensis is known as Bloodroot, Puccoon, Tetterwort, etc. and is an herb native to North America. The plant and its juices have been used for various purposes during pre-history as well as written history. It has been used as a natural historic folk remedy medicine. The plant has been generally used whole either undried (fresh) or dried. The usual procedure is to powder the dried plant and mix it with a carrier. This folk remedy has been tried for such things as asthma, bronchitis, dysentery, ringworm, and a substantial list of other ailments.

Sanguinarine, chelerythrine, and other benzophenanthridine alkaloids are known alkaloids defined as isoquinolines. Plant sources for these alkaloids fall into various species; the Papaveraceae, Fumariaceae, and Rutaceae families. Recoveries of these alkaloids from *Sanguinaria Canadensis L.* and Macleaya species are described in U.S. Pat. Nos. 4,145,412; 4,406,881; 4,517,172; 4,590,061; 4,599,228; 4,683,133; 4,689,216; 4,767,861; and 4,769,452. Production of these alkaloids from plant tissue culture has been described in *Plant Cell Reports* (1988) 7:410–413.

Purification of the benzophenathridine alkaloids into individual alkaloids without using known chromatographic methods is also described in the foregoing U.S. patents.

The use of an extract containing these benzophenanthridine alkaloids from Sanguinaria Canadensis L. as an ingredient in an oral cleansing preparation is also disclosed in the foregoing U.S. patents.

Other uses for the extract of Sanguinaria Canadensis L. are reported as a plaque disclosing agent in U.S. Pat. Nos. 4,517,172 and 4,590,061.

It is known that mouthrinses and dentifrices containing sanguinaria extract are effective anti-plaque and anti-gingivitis agents. They are also effective against oral malodor and calculus. The alkaloid extract when made into an oral rinse, dentifrice, or oral care product is an excellent breath freshener, and also an anti-plaque and anti-gingivitis agent. European Patent 396,232 discloses an antimicrobial mouthrinse containing sanguinaria which is stabilized by the presence of an orally acceptable buffer system such as sodium citrate and citric acid, buffered to acid pH. Although mouthrinses of this type are quite effective, there is still a need for improved mouthrinses.

The present inventors have unexpectedly found that sanguinaria based mouthrinses utilizing mixtures of specific surfactants exhibit improved anti-microbial efficacy and stability, especially when compared to mouthrinses disclosed in European Patent 396,232.

SUMMARY OF THE INVENTION

In accordance with the present invention, novel mouthrinses containing sanguinaria extract of superior antimicrobial activity and stability are obtained using selective combinations of surfactants incorporated in the mouthrinse composition, the surfactant combination being comprised of an amidobetaine and a block copolymer of polyoxyethylene and polyoxypropylene.

As will hereafter be demonstrated, the use of the specific surfactant combination of the present invention results in a sanguinaria based mouthrinse of improved antimicrobial activity and stability especially when compared to sanguinaria mouthrinses in which the combination is absent. The improved results achieved with the amidobetaine/polyoxyethylene-polyoxypropylene block polymer surfactant combination is particularly unexpected in view of the fact that EP 396,232 teaches that the presence of a polyoxyethylene-polyoxypropylene block copolymer non-ionic surfactant by itself in sanguinaria mouthrinses results in decreased stability of the mouthrinse.

DETAILED DESCRIPTION OF THE INVENTION

The sanguinaria mouthrinses of the present invention are alcoholic aqueous mouthrinses which are usually made up on the basis of the other components with water being the amount necessary to make the composition up to 100%. The water utilized is preferably a deionized or distilled water and comprises about 70 to about 95 percent by weight and preferably about 75 to 90 percent by weight of the mouthrinse.

The alcohol component of the mouthrinse is a non-toxic alcohol such as ethanol, and comprises about 5 to about 25% by weight and preferably about 5 to about 15% by weight of the mouthrinse.

The present invention provides an alcohol-containing aqueous based mouthrinse containing a small but effective amount of one or more benzophenathridine alkaloids and preferably about 0.01 to about 0.2% by weight of the alkaloid, and between about 0.1% and 3% of a combination of a non-ionic polyoxyethylene-polyoxypropylene block polymer and an amidobetaine, the weight ratio of polymer to betaine being in the range of about 1:10 to 1:2 and preferably about 1:5 to about 1:2.

Illustrative of the benezophenanthridine alkaloids which are useful in the composition of this invention include sanguinarine, chelerythrine, sanguilutine, chelitutine, chelirubine, and sanguirubine.

Polyoxypropylene-polyoxyethylene block copolymers used in the compositions of the present invention have the formula:

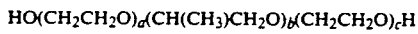

$$HO(CH_2CH_2O)_a(CH(CH_3)CH_2O)_b(CH_2CH_2O)_cH$$

wherein a, b, and c are integers reflecting the respective polyethylene oxide and polypropylene oxide blocks of said polymer. The polymer preferably has a molecular weight of between about 1,000 and 4,000. These block polymers are well known to the art and are available under the trademark "Pluronics". The block copolymers are formed by condensing ethylene oxide with a hydrophobic base formed by the condensation of propylene oxide with propylene glycol.

The poly(oxyethylene)-poly(oxypropylene) block copolymer is generally incorporated in the mouthrinse compositions of the present invention at a concentration of about 0.05 to about 0.2% by weight of the total weight of the mouthrinse.

The amidobetaines used in the preparation of the mouthrinse compositions of the present invention have the general formula:

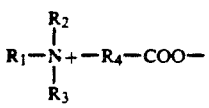

wherein $R_1$ is

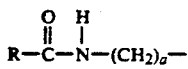

R is an alkyl group having about 10 or 20 carbon atoms and a is the integer 1 to 3; $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Amidobetaines useful in the practice of the present invention include cocoamidoethyl betaine, cocoamidopropyl betaine, lauramidopropyl betaine and the like.

The amidobetaine is generally incorporated in the mouthrinse compositions of the present invention at a concentration of about 0.1 to about 1% by weight and preferably about 0.3 to about 0.5% by weight of the mouthrinse.

It is critical to the practice of the present invention that the combination of the poly(oxyethylene)-poly(oxypropylene) block copolymer and amidobetaine be incorporated in the mouthrinse. In the absence of either of these surfactants reduced antimicrobial activity and/or stability are observed. Generally, the combination of amidobetaine and poly(oxyethylene)-poly(oxypropylene) block copolymer are present in the rinse at a concentration of about 0.1 to about 1% by weight and preferably about 0.20 to about 0.75 percent by weight. The mouthrinse compositions preferably contain humectants such as glycerine in amounts of about 2 to about 15% by weight with compositions containing between about 2% and 8% by weight being preferred. The glycerine functions to supply "body" to the composition. Other adjuvants such as gelling agents like sodium carboxymethyl cellulose may also be incorporated in the mouthrinse to supply body to the composition. The gelling agent is incorporated in the rinse at a concentration of about 0.05 to about 1% by weight and preferably about 0.1% to about 0.3% by weight.

The mouthrinse compositions may also contain adjuvants to provide color, additional flavoring if desired, and sweetening effects. Color is typically added in an amount up to about 0.01%. Additional flavor or sweetener, is preferably added in small amounts, e.g., about 0.02 to 1% by weight.

The type of sweetening agents suitable for this application include, aspartame, acesulfame K, xylitol, sodium cyclamate, and saccharin. Flavoring agents used in the compositions of this invention include phenolic, cinnamon, and mint flavors.

A buffer system is also included in the mouthrinse composition of the present invention which is capable of maintaining the pH of the compositions in the range of about 4.0 to 5.6. In this pH range the maximum stability of the compositions is attained.

Buffer systems which are useful in the compositions of the invention include sodium citrate/citric acid, sodium acetate/acetic acid, sodium phosphate/phosphoric acid, sodium succinate/succinic acid, sodium lactate/lactic acid, and sodium propionate/propionic acid.

The mouthrinse composition of the present invention is prepared by combining the specified components in an amount of water sufficient to bring the total of the components to 100%. The sequence of addition of the various components is not critical, except that any flavor should be added first to the alcohol before the addition of any of the other ingredients to insure solubility and gelling agents such as sodium carboxycellulose should be added last to avoid premature precipitation. Generally, it is preferred to mix the alcohol soluble components, e.g. flavor agents, in the alcohol and then add water. Components of the mouthrinse which have greater solubility in water than alcohol are preferably added to the water before it is admixed with the alcohol or added to the composition after the water addition.

The following Examples are further illustrative of the present invention but the invention is not limited thereto. All amounts and percentages throughout the specification and in the claims are by weight unless otherwise indicated.

EXAMPLE I

An aqueous mouthrinse hereinafter referred to as "Example I Rinse" was prepared using the ingredients listed below in the amounts stated:

| INGREDIENT | % BY WEIGHT |
| --- | --- |
| Ethanol | 10.000 |
| Phenolic flavor | 0.150 |
| Na saccharin | 0.075 |
| Pluronic F87[2] | 0.200 |
| Glycerin | 3.000 |
| Sorbitol | 3.000 |
| Tegobetaine L5351[1] | 0.400 |
| Purified Water | 79.933 |
| Citric Acid | 0.038 |
| Na citrate | 0.004 |
| Sanguinaria Premix (1%) | 3.000 |
| Na carboxymethyl cellulose | 0.200 |
| TOTAL | 100.000 |
| pH 4.4–4.6 | |

[1]Tegobetaine L5351 is cocoamido propyl betaine commercially available from Goldschmidt Chemical Corp.
[2]Pluronic F-87, commercially available from BASF-Wyandotte is a polyoxyethylene-polyoxypropylene block polymer.

The mouthrinse was prepared in the following manner:

The ingredients were added to a mixing vessel in the order listed above, 5 minutes mixing time being allowed between each addition, and sodium carboxymethyl cellulose being added last. It was determined that unless the sodium carboxymethyl cellulose was added last, it would precipitate from the solution. After the addition of the last ingredient, sodium carboxymethyl cellulose, the entire formula was mixed for an additional 45 minutes.

For purposes of comparison, the procedure of Example I was followed to prepare the following comparative mouthrinse, hereinafter referred to as "Comparative Rinse":

| INGREDIENTS | PERCENT |
| --- | --- |
| Ethanol | 9.855 |
| Sodium Saccharin | 0.076 |
| Pluronic F87 | 0.200 |
| Mint Flavor | 0.200 |
| Polysorbate 80* | 0.400 |

| -continued | |
|---|---|
| INGREDIENTS | PERCENT |
| Glycerin | 3.000 |
| Purified Water | 81.773 |
| Zinc Chloride | 0.200 |
| Sodium Citrate | 0.280 |
| Citric Acid | 0.016 |
| Sanguinaria premix (1%) | 3.000 |
| Purified Water | 1.000 |
| TOTAL | 100.000 |

*Polyoxyethylene derivative of fatty acid partial ester of sorbitol anhydride

Antimicrobial activity of the mouthrinse was determined in accordance with a short interval killing time test which was used to determine the in vitro antimicrobial activity of compounds. In this test, a small (1 ml) sample of the mouthrinse was mixed with a bacterial inoculum of *Actinomyces viscosus* T14V and allowed to stand at room temperature for 60 seconds after which the surviving bacteria were enumerated. Bacterial reduction in percent compared to a water control was used as the basis for expressing activity. By this test, the Example I Rinse showed a 99.99% reduction in bacterial count after 1 minute.

Release of sanguinaria to teeth was determined by an in vitro assay using disks of hydroxyapatite (HAP), a mineral phase of teeth. The protocol for this test is fully described in Nabi et al, *American Journal of Dentistry*, Vol. 2, Special Issue, September, 1989. The test is designed to mimic the in vivo situation wherein active agents are taken up onto tooth surfaces. In this test, a sintered HAP disk (0.2 g) was treated with saliva and incubated overnight at 37° C. After this treatment, the saliva was removed and the disks treated with 1 ml of the mouthrinse and incubated at 37° C. for 60 minutes. The incubated disk was treated with 1% HCl-methanol to extract the sanguinaria from the rinse solution. After extraction, the 1% HCl methanol solution was transferred to HLPC vials for determination of sanguinaria concentration.

By this test, the amount of sanguinaria bound to the HAP disk was determined to be 126 ppm sanguinaria/gm disk.

By way of contrast, the Comparative Rinse was found to release 90.5 ppm sanguinaria/gm disk.

To determine the efficacy of the Example I Rinse against microorganisms found in dental plaque, a protocol similar to that described in Gaffar et al, *American Journal of Dentistry*, Vol. 3, Special Issue, September 1990, pp 57-514, was employed using two germanium prisms, 50×20×1 mm, as test plates to allow for internal reflection infrared analysis which measures the total bacteria or plaque deposited on the plates. The plates were initially cleaned with detergent solution using a medium long camel brush hair (which was treated with concentrated alcoholic-KOH). The plates were then rinsed with copious amounts of deionized distilled water, followed by rinsing with methanol and dried under atmospheric conditions in a vertical position. The procedure resulted in plate surfaces having wetting properties similar to that of the human teeth enamel.

Prethickness of the plates was measured using a Gaertner Auto Gain Ellipsometer. The plates were placed in a flow cell of the type disclosed in U.S. Pat. No. 4,175,233 and whole saliva, supplemented with 10% trypticase soy broth (TSB), was circulated through the flow system at a flow rate of 1 ml/min for 72 hours, with TSB-saliva changed every 24 hours. The plates were pulsed twice daily with Example I Rinse at a flow rate of 10 ml/min for 1 minute. The results of these tests designated ("Ex I") are recorded in Table I below.

For purposes of comparison, the above procedure was repeated with the exception that the plates were pretreated with the Comparative Rinse. The results of these tests are also recorded in the Table I below designated ("Compar").

In Table I, Total Plaque was determined using the summation of the relative absorbance at 3300, 1650, 1540 and 1080 cm−1. Bacterial and extracellular polysaccharides (ex-CHO) were the relative absorbance at 1540 and 1080 cm−1 respectively and Plaque Area is the total area in cm² of the spectra after spectral manipulation—baseline from 4000—910 cm−1

TABLE I

| RINSE | TOTAL PLAQUE | % RED | BACTERIA | % RED | ex-CHO | % RED | PLAQUE AREA | % RED |
|---|---|---|---|---|---|---|---|---|
| Compar. | 2.665 | — | 0.732 | — | 0.2735 | — | 498.2 | — |
| EX I | 0.930 | 65.1 | 0.246 | 66.4 | 0.0925 | 66.2 | 200.2 | 59.8 |

*Reduction

Reference to the Table indicates that the mouthrinse of the present invention effects a substantial improvement in reducing bacterial and plaque activity, especially when compared to the Comparative Rinse.

EXAMPLE II

To determine the stability of the mouthrinse composition of the present invention, that is, the ability of the rinse to withstand a decrease in efficacy due to premature precipitation of the available sanguinaria in the rinse, the rinse was aged for 2.5 weeks at 73°-120° F. and analyzed for sanguinaria concentration by HPLC.

For purposes of comparison, the Comparative Rinse was also aged under identical conditions. The results of these aging tests are recorded in Table II below.

TABLE II

| Stability of Sanguinaria in Mouthrinse | | | | | |
|---|---|---|---|---|---|
| | Initial | | Aged 2.5 Weeks Sang % | | |
| | Sang % | pH | 73° F. | 100° F. | 120° F. |
| Example I Rinse | 0.034 | 4.4–4.6 | 0.033 | 0.033 | 0.033 |
| Compar Rinse | 0.034 | 4.51 | * | * | * |

*precipitate visible within one week

The results recorded in Table II indicate the stability of the mouthrinse with regard to sanguinaria content is substantially greater in the Example I Rinse than in the Comparative Rinse.

What is claimed is:

1. A mouthrinse composition comprising about 0.01 to about 0.2% by weight of a benzophenanthridine alkaloid in an aqueous solution and a surfactant combination of an amido betaine and a block polymer of polyoxyethylene and polyoxypropylene, the surfactant combination being present in the composition at a concentration of about 0.1 to about 3.0% by weight, the weight ratio of betaine to polymer being in the range of about 1:10 to about 1:2.

2. The mouthrinse composition of claim 1, wherein the alkaloid is selected from the group consisting of water soluble salts of sanguinarine, chelerythrine, sanguilutine, chelilutine, chelirubine, and sanguirubine.

3. A composition in accordance with claim 1 wherein the amidobetaine has the general formula:

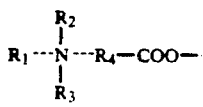

wherein $R_1$ is

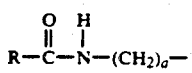

R is an alkyl group having about 10 or 20 carbon atoms and a is an integer of 1 to 3; $R_2$ and $R_3$ are each alkyl groups having 1 to 3 carbons and preferably 1 carbon; $R_4$ is an alkylene or hydroxyalkylene group having from 1 to 4 carbon atoms, or a hydroxyl group.

4. The mouthrinse composition of claim 1, wherein the polyoxyethylene-polyoxypropylene block polymer has the general formula:

wherein a, b, and c are integers reflecting the respective polyethylene oxide and polypropylene oxide blocks of the polymer.

5. The mouthrinse composition of claim 1 wherein the alkaloid is present in the rinse at a concentration of about 0.01 to about 0.2% by weight.

6. The composition of claim 1 wherein the alkaloid is sanguinarina extract.

7. The composition of claim 1 wherein the amido betaine is cocoamido propyl betaine.

8. The composition of claim 1 wherein the combination of amido betaine and polyoxyethylene-polyoxypropylene block polymer is present in the rinse at a concentration of about 0.1 to about 2% by weight, the weight ratio of betaine to polymer being in the range of about 5:1 to about 2:1.

9. The composition of claim 1 further comprising about 5 to about 25% by weight ethyl alcohol, about 2 to 15% by weight of humectant, about 0.05 to about 1% by weight gelling agent, about 0.02 to about 1% by weight sweetening agent, about 0.05 to about 0.4% by weight flavoring agent, and sufficient buffering agent to maintain the pH in the range of about 4.0 to about 5.6.

* * * * *